United States Patent [19]
Lorinez et al.

[11] Patent Number: 5,981,179
[45] Date of Patent: Nov. 9, 1999

[54] CONTINUOUS AMPLIFICATION REACTION

[75] Inventors: Attila T. Lorinez, North Potomac; Abel DeLaRosa, Bethesda, both of Md.

[73] Assignee: Digene Diagnostics, Inc., Beltsville, Md.

[21] Appl. No.: 08/527,864

[22] Filed: Sep. 14, 1995

Related U.S. Application Data

[63] Continuation-in-part of application No. 08/183,154, Jan. 18, 1994, Pat. No. 5,570,099, which is a continuation of application No. 07/792,585, Nov. 14, 1991, abandoned.

[51] Int. Cl.$^6$ ............... C12P 19/34; C07H 21/02; C07H 21/04; C07H 21/00
[52] U.S. Cl. ............... 435/6; 435/91.2; 435/183; 435/195; 536/23.1; 536/25.32; 536/24.3; 536/22.1
[58] Field of Search ............... 435/91.2, 6, 183, 435/195; 536/23.1, 25.32, 24.3, 22.1

[56] References Cited

U.S. PATENT DOCUMENTS

| | | | |
|---|---|---|---|
| 5,130,238 | 7/1992 | Malek et al. | 435/6 |
| 5,399,491 | 3/1995 | Kacian et al. | 435/91.21 |
| 5,498,531 | 3/1996 | Jarrell | 435/91.31 |
| 5,573,914 | 11/1996 | Love | 435/6 |

FOREIGN PATENT DOCUMENTS

| | | |
|---|---|---|
| 2039388 | 10/1991 | Canada . |
| 310 229 | 4/1989 | European Pat. Off. . |
| 369 775 | 5/1990 | European Pat. Off. . |
| 587 298 A2 | 3/1994 | European Pat. Off. . |
| 329 822 B1 | 6/1994 | European Pat. Off. . |
| WO 88/10315 | 12/1988 | WIPO . |
| WO 89/06700 | 7/1989 | WIPO . |
| WOA 89 06700 | 7/1989 | WIPO . |
| WO A 91 04340 | 4/1991 | WIPO . |
| WO A 93 05184 | 3/1993 | WIPO . |
| WOA 93 10263 | 5/1993 | WIPO . |
| WO A 93 24658 | 12/1993 | WIPO . |
| WO A 94 03472 | 2/1994 | WIPO . |
| WO A 95 08626 | 3/1995 | WIPO . |

OTHER PUBLICATIONS

Zhou, W. et al., "T7 RNA Polymerase Bypass of Large Gaps on the Template Strand Reveals a Critical Role of the Nontemplate Strand in Elongation", *Cell*, vol. 82, Aug. 25, 1995, pp. 577–585.

The International Search Report, Jan. 17, 1997, 6 pgs.

*Primary Examiner*—Stephanie W. Zitomer
*Assistant Examiner*—Joyce Tung
*Attorney, Agent, or Firm*—Morgan & Finnegan, L.L.P.

[57] ABSTRACT

Continuous amplification reaction provide a method of amplifying a specific nucleic acid without the need to cycle a reaction. The method produces RNA transcripts which can be detected by a variety of methods. Amplification and detection kits are also provided.

26 Claims, 6 Drawing Sheets

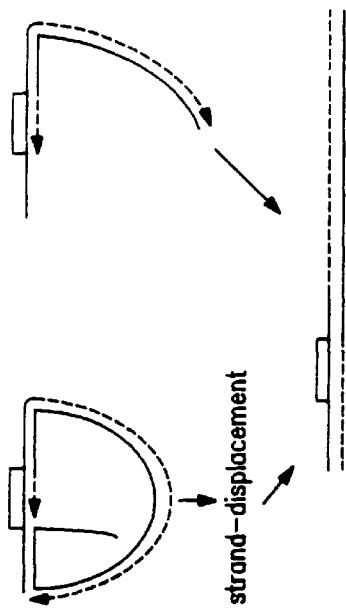
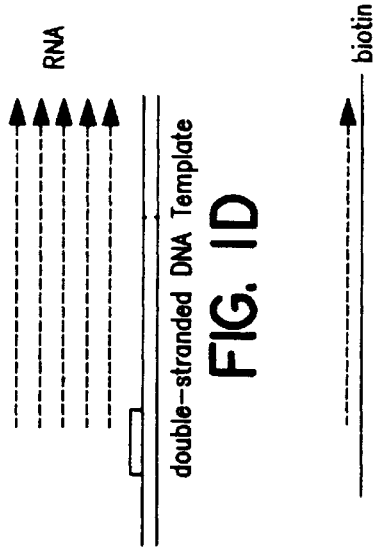
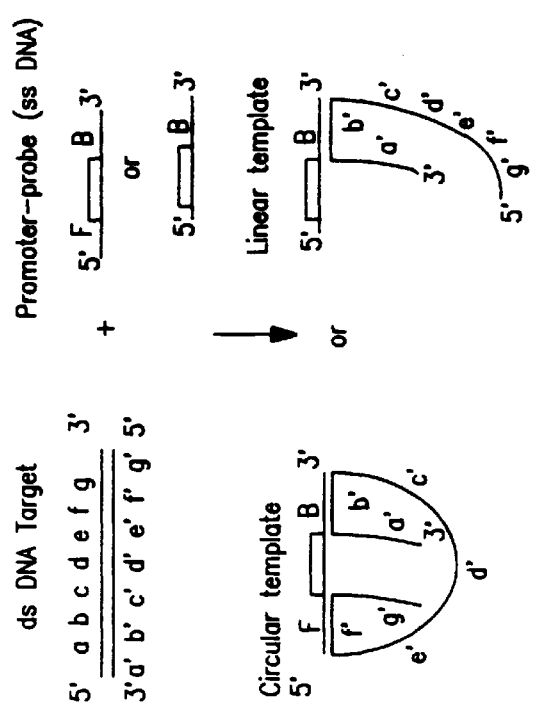
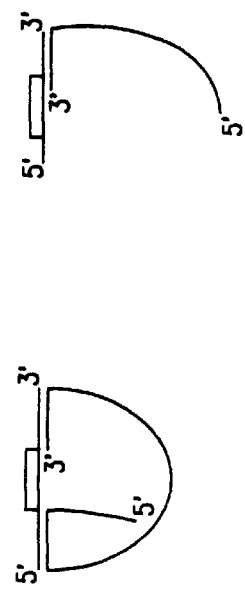

CONTINUOUS AMPLIFICATION REACTION

CROSS-REFERENCES TO RELATED APPLICATION

This application is a continuation-in-part of U.S. patent application Ser. No. 08/183,154 filed Jan. 18, 1994 now U.S. Pat. No. 5,570,099, which is a continuation application of U.S. patent application Ser. No. 07/792,585 filed on Nov. 14, 1991, now abandoned.

FIELD OF INVENTION

This invention relates to the field of nucleic acid amplification reactions in general and more particularly relates to a continuous amplification reaction, and reaction generating specific amplified RNA products from a DNA target.

BACKGROUND OF THE INVENTION

The amplification and detection of specific nucleic acid sequences present in minute amounts is an increasingly important technique for identifying and classifying microorganisms, diagnosing infectious diseases, detecting and characterizing genetic abnormalities, identifying genetic changes associated with cancer, studying genetic susceptibility to disease, and measuring response to various types of treatment. Such procedures have also found expanding uses in detecting and quantitating microorganisms in foodstuffs, environmental samples, seed stocks, and other types of material where the presence of specific microorganisms may need to be monitored. Other applications are found in the forensic sciences, anthropology, archaeology, biology and clinical medicine where measurement of the relatedness of nucleic acid sequences has been used to identify criminal suspects, resolve paternity disputes, construct genealogical and phylogenetic trees, aid in classifying a variety of life forms, and identify disease states.

A common method for detecting and quantitating specific nucleic acid sequences is nucleic acid hybridization. The sensitivity of nucleic acid hybridization assays is limited primarily by the specific activity of the probe, the rate and extent of the hybridization of the probe, and the sensitivity with which the label can be detected. The most sensitive procedures may lack many of the features required for routine clinical and environmental testing, such as speed, economy and convenience. Furthermore, their sensitivities may not be sufficient for many desired applications.

As a result of the interactions among the various components and component steps of this type of assay, there is often an inverse relationship between sensitivity and specificity. Thus, steps taken to increase the sensitivity of the assay (such as increasing the specific activity of the probe) may result in a higher percentage of false positive test results. The linkage between sensitivity and specificity has been a significant barrier to improving the sensitivity of hybridization assays. One solution to this problem would be to specifically increase the amount of target sequence present using an amplification procedure. Amplification of a unique portion of the target sequence without amplification of a significant portion of the information encoded in the remaining sequences of the sample could give an increase in sensitivity while at the same time not compromising specificity.

Amplification has been used to increase the sensitivity of nucleic acid assays. One common method for specifically amplifying nucleic acid sequences termed the "polymerase chain reaction" or "PCR" has been described by Mullis et al. (See U.S. Pat. Nos. 4,683,202 and 4,683,195 and European patent applications 86302298.4, 86302298.4, and 87300203.4 and *Methods in Enzymology,* Volume 155, 1987, pp. 335–350.) The procedure uses repeated cycles of primer dependent nucleic acid synthesis occurring simultaneously using each strand of a complementary sequence as a template. Therefore, at least two primers are required in PCR. The sequence amplified is defined by the primer molecules that initiate synthesis. The primers are complementary to the 3'-end portion of a target sequence or its complement and must complex with those sites in order for nucleic acid synthesis to begin. After extension product synthesis, the strands are separated, generally by thermal denaturation, before the next synthesis step. In the PCR procedure, copies of both strands of a complementary sequence are synthesized.

The requirement of repeated cycling of reaction temperature between several different and extreme temperatures is a disadvantage of the PCR procedure.

The PCR procedure has been coupled to RNA transcription by incorporating a promoter sequence into one of the primers used in the PCR reaction and then, after amplification by the PCR procedure for several cycles, using the double-stranded DNA as template for the transcription of single-stranded RNA. (see e.g., Murakawa et al. DNA 7:827-295 (1988)). Other methods of amplifying nucleic acid sequences are also commercially available. These methods include the ligation amplification reaction (LCR), and the transcription-based amplification reaction. Ligation amplification reaction is described by Wu, D. Y and Wallace, R. B, *Genomics* 4:560–569 (1989) and Barringer, K. J., et al., *Gene* 89:117–122 (1990). Transcription-based amplification reaction is described by Kwoh, D. Y., et al., *Proc. Natl. Acad. Sci. USA* 86:1173–1177 (1989). These methods have the advantages of high sensitivity, but the disadvantages of being prone to false-positive results from reaction product contamination.

It is therefore an object of the present invention to amplify a target nucleic acid by continuous amplification reaction, which does not require repeated cycles of amplification and produces many RNA copies of the target sequence.

Another object of the present invention relates to detection of minute amounts of nucleic acids through use of a continuous amplification reaction (also referred to herein as "CAR").

Yet another object of the invention is to indirectly amplify a target DNA signal by synthesizing and detecting multiple copy RNA molecules.

It is a further object of the present invention to provide a cost-effective, sensitive, solution hybridization assay for RNA transcripts produced by CAR.

SUMMARY OF THE INVENTION

The present invention provides an amplification method, referred to herein as continuous amplification reaction ("CAR"). CAR is capable of producing detectable amounts of RNA transcripts from a minute amount of starting target region of a nucleic acid. This in vitro method for the enzymatic synthesis of RNA is based on an oligonucleotide primer containing a RNA polymerase promoter. This oligonucleotide is referred to herein as a promoter-primer.

The promoter portion of the promoter-primer may be flanked on either or both sides with regions homologous to one or two separate regions on the target nucleic acid molecule. Alternatively, the promoter-primer of the present invention may be a partially double-stranded oligonucleotide wherein it is double stranded within the promoter portion and single stranded within the primer portion of the oligonucleotide. A third alternative provides a promoter-primer which is a single oligonucleotide strand which is double stranded within the promoter region due to a stem loop formation in the oligonucleotide.

When the promoter is located in the center of the promoter-primer, hybridization between the promoter-primer and the target region of a nucleic acid forms a circular template-primer hybrid. Alternatively, the primer portion can be located downstream of the promoter on the promoter-primer in which case hybridization to the target region of a nucleic acid forms a linear structure.

Any nucleic acid may be amplified by the method of the present invention. A nucleic acid comprises a string of nucleotides of variable length. The nucleic acid may be amplified in its entirety or a portion of the nucleic acid may be selected for amplification. In either case, the region of the nucleic acid containing the sequence(s) required for promoter primer hybridization and the sequence selected for transcription are referred to herein as the target region.

In the case where a portion of a nucleic acid is the target region, the 3' end of the nucleic acid may extend beyond the target region and such 3' flanking sequence is removed in a trimming step. This step may be accomplished by 3'-5' exonuclease digestion which may comprise a separate enzyme or the exonuclease activity associated with many nucleic acid polymerases. Alternatively, a unique restriction site may be created by hybridization of the denatured, single-stranded nucleic acid sequence to a trimming probe. The trimming probe comprises a sequence complementary to the 3' junction of the target region. The 3' junction of the target region comprises a sequence complementary to a portion of the target region and a sequence complementary to a region of the nucleic acid located 3' to the target region. Hence, restriction digestion of the site created by this hybrid molecule will generate a trimmed 3' end, wherein the product is ready for hybridization with a promoter-primer. Optionally, the trimming-probe may carry at least one ligand, capable of being captured on a solid matrix.

Under either of these conditions, the template-promoter primer hybrids are extended by the enzymatic activity of a nucleic acid polymerase. It may also be desirable to incorporate modified nucleotides into the 3' portion of the promoter-primer, such that the exonucleolytic activity associated with many nucleic acid polymerases will not digest any part of the promoter-primer. After polymerase extension along the length of template and promoter region, a double-stranded nucleic acid is formed. This product is subjected to transcription using, for example, RNA polymerase. In this way, a template DNA can be indirectly amplified without the need to carry out any cycled reaction. Such transcripts can be detected by various methods including a hybrid-capture system.

In another aspect of the present invention, CAR provides an amplification reaction using a partially double-stranded promoter-primer which is double stranded in the promoter portion and single stranded in the primer portion. Prior to hybridization with the promoter primer, any 3' flanking sequence is removed. The removal or "trimming" of the 3' flanking sequence may be carried out with, for example a trimming probe, which removes the any single stranded sequences 3' of the target region. Upon hybridization of this promoter primer to target DNA, transcription is carried out. Optionally, a ligation reaction may be carried out to fill the gap between the promoter and the template. Further, it may be desired to produce a fully double stranded transcription template by first extending the partially double stranded hybrid with a nucleotide polymerase, preferably a DNA polymerase.

Kits are provided for screening samples for specific nucleic acid targets via CAR-produced RNA transcripts.

BRIEF DESCRIPTION OF THE DRAWING

FIG. 1 is a schematic diagram illustrating CAR. Step A shows the hybridization of a double stranded target DNA molecule with a single stranded promoter-primer. Step B shows the use of exonuclease, specific for 3'→5' cleavage which digests the excess single-stranded 3' ends of the DNA. Step C shows extension reactions using DNA polymerase, extending the 3' end of the promoter-probe and target DNA thereby producing a double-stranded DNA having a functional RNA polymerase promoter at its 5' end. Step D shows a transcription reaction with an RNA polymerase. Step E shows transcript hybridization to a DNA probe making an RNA/DNA hybrid, which provides one method of detecting CAR-produced transcripts.

DETAILED DESCRIPTION OF THE INVENTION

Figure 2:
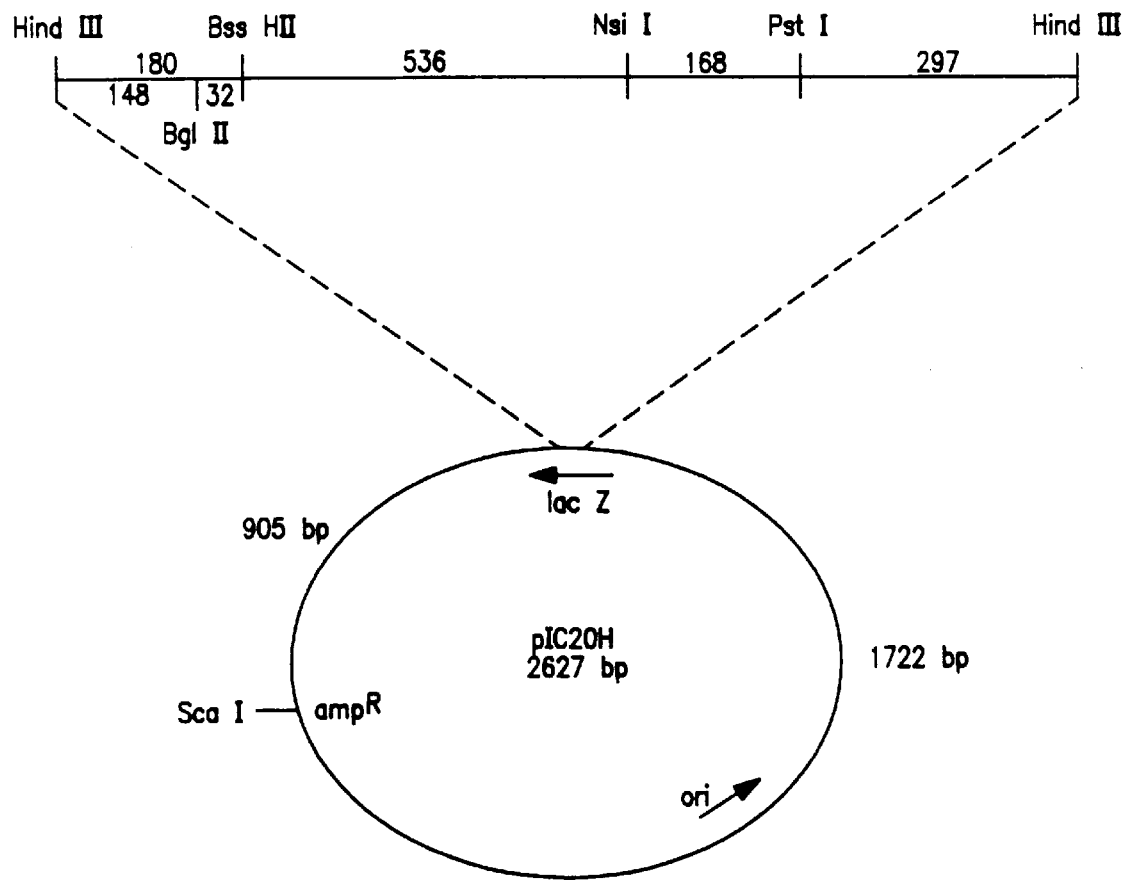
FIG. 2: Plasmid, illustrating the HIV-1 DNA region, with multiple internal restriction sites, used to generate CAR targets.

The present invention relates to the amplification of a target nucleic acid. A method of amplification according to the present invention comprises denaturing a target nucleic acid forming a single-stranded nucleic acid strand; hybridizing said single-stranded nucleic acid to a promoter-primer forming a hybrid; trimming back the 3' end of the nucleic acid strand; extending the 3' end of promoter-primer and the trimmed 3' end of target strand with a nucleic acid polymerase forming a double-stranded nucleic acid having a functional RNA polymerase promoter; transcribing the double-stranded nucleic acid producing many RNA copies of the target sequence.

The ability to introduce a functional promoter to a specific site, in a target-dependent manner, allows the generation of at least 100 RNA transcripts from each specific nucleic acid target molecule. Coupling the CAR method with a specific and highly sensitive detection system, such as the Hybrid Capture system as described herein, permits the detection assay to be coupled with two levels of specificity. The first level of specificity is provided by targeting specific regions of a nucleic acid for amplification using the promoter-primer and the second level of specificity is achieved through use of a probe to detect the newly transcribed RNA. The ability to indirectly amplify DNA target molecules via CAR inherently augments the level of detection of specific DNA sequences. The present invention provides the CAR approach, which allows the detection limits of specific nucleic acid sequences to be lowered.

Any source of nucleic acid, in purified or non-purified form, can be utilized as the test sample. For example, the test sample may be a food or agricultural product, or a human or veterinary clinical specimen. Typically, the test sample is a biological fluid such as urine, blood, plasma, serum, sputum or the like. Alternatively the test sample may be a tissue specimen suspected of carrying a nucleic acid of interest. The nucleic acid to be detected in the test sample is DNA or RNA, including messenger RNA, from any source, including bacteria, yeast, viruses, and the cells or tissues of higher organisms such as plants or animals. Methods for the extraction and/or purification of such nucleic acids have been described, for example, by Maniatis, et al., Molecular Cloning: A Laboratory Manual (New York, Cold Spring Harbor Laboratory, 1982).

The nucleic acid sequence to be detected in the test sample may be present initially as a discrete molecule so that the sequence to be detected constitutes the entire nucleic acid, or may only be a component of a larger molecule. It is not necessary that the nucleic acid sequence to be detected be present initially in a pure form. The test sample may contain a complex mixture of nucleic acids, of which the nucleic acid sequence to be detected may correspond to a gene of interest contained in total human genomic DNA, or a portion of the nucleic acid sequence of a pathogenic organism which organism is a minor component of a clinical sample.

The term "oligonucleotide" as the term is used herein refers to a nucleic acid molecule comprised of two or more deoxyribonucleotides or ribonucleotides. A desired oligonucleotide may be prepared by any suitable method, such as purification from a naturally occurring nucleic acid, or de novo synthesis. Examples of oligonucleotides are probes and promoter-primers described herein.

The term "RNA transcript" as the term is used herein refers to a ribonucleic acid molecule synthesized by an RNA polymerase enzyme under the control of the promoter-primer. The RNA transcript of a specific nucleic acid sequence is either homologous or complimentary to that sequence.

Continuous Amplification Reaction ("CAR") is capable of amplifying a nucleic acid template in order to produce a detectable amount of RNA product. The amplification method can detect as little as 10–100 molecules of nucleic acid. The method uses an oligonucleotide comprising at least one segment complementary to one strand of a target sequence and a segment containing a promoter. This oligonucleotide primer, when hybridized to a strand of a template, preferably the anti-sense strand, and extended can generate a copy of the target nucleic acid with the capability of transcription via the added promoter sequence. The promoter is added to the 5' end of the strand to be transcribed. If the anti-sense strand of a target region is used for the hybridization step, the promoter is added to the 5' end of the coding strand of the target nucleic acid.

In one preferred embodiment, a nucleic acid and a promoter-primer are hybridized. The primer portion of the promoter-primer is designed to be complementary to non-contiguous portions of the target region. For example portions at both ends of the target region of the nucleic acid may be selected for hybridization. In addition, the promoter-primer is designed to contain a promoter sequence for an RNA polymerase. Upon hybridization, the primer portions of the promoter-primer link the 5' and 3' end portions of the target region of nucleic acid, such that the promoter sequence portion is sandwiched between the two hybridized end sequences. The result of this hybridization is the formation of a circle. Hereinafter, this embodiment is referred to as "circular CAR". In the case where the target region is a segment of a larger nucleic acid hybridization of the promoter-primer results in the formation of a circle with at least one dangling end.

Any single stranded 3' sequence flanking the target region may then be trimmed back to produce a 3' end of the target sequence which is flushed with the hybridized promoter-primer. "Flushed" as the term is used herein refers to a double-stranded end with no single stranded sequence at the end of the target nucleic acid: For example, a 3' flushed sequence may be produced by the triming step. Simultaneous with or subsequent to the trimming back step is the extension step which extends the 3' ends of the hybrid structure via a nucleic acid polymerase forming an extension product. The nucleic acid polymerase extends the 3' end of the promoter-primer along the template to form a double stranded intermediate. The polymerase also extends the trimmed 3' end of the template thereby extending the nucleic acid so that the resulting intermediate product will be double-stranded along its entire length and carry a functional transcriptional promoter. Finally, the double-stranded extension product is transcribed by an RNA polymerase, generating multiple RNA transcripts from each extension product. The promoter, originally part of the promoter-primer, facilitates the action of the RNA polymerase, resulting in the production of many RNA transcripts from the copied target nucleic acid.

Another embodiment of the present invention relates to the use of an oligonucleotide promoter primer, wherein the primer portion is complementary to a 3' portion of the target region in a nucleic acid sequence. This embodiment is hereinafter referred to as "linear CAR". The promoter portion of the promoter-primer is located at the 5' end. After hybridization is complete, 3' single stranded sequences flanking the target region may be trimmed back to produce a 3' flushed end. Simultaneous with or subsequent to removal of the single stranded 3' flanking sequence, extension is carried out via the activity of a nucleic acid polymerase, producing an extension product carrying the newly added promoter region. The resulting double stranded nucleic acid is then transcribed with an RNA polymerase, facilitated by the newly added promoter sequence.

Yet another embodiment of the present invention, which is referred to as double-stranded-CAR ("ds-CAR"), relates to the use of a partially double-stranded promoter-primer (referred to as "ds-promoter-primer"), wherein the promoter-primer is double-stranded within the promoter portion and is single-stranded within a region downstream to the promoter which is complementary to the 3' end of the target region.

In one embodiment of ds-CAR, upon hybridization, the 3' end of the DNA target directly abuts the 5' end of the short strand of the ds-promoter-primer. This hybrid structure may be directly subjected to transcription. Optionally, ligase may then be reacted with this hybrid forming a continuous, partially double-stranded template which is also transcription-ready. Yet another optional step may include extending either of the above described partially double stranded molecules (either ligated or non-ligated) with a DNA polymerase, thereby producing a fully double stranded template, also ready for transcription (see, for example, Zhou, et al. 1995 *Cell* 82, 577–585). Transcription is then carried out using an RNA polymerase to produce many RNA transcripts.

The partially double stranded promoter-primer of the present invention may be made up of multiple oligonucleotides, which have been hybridized or covalently linked. Alternatively the ds-promoter-primer may be a single oligonucleotide strand with intramolecular folding capabilities such that a stem-loop structure is formed, wherein the stem is formed within the promoter portion while the primer portion remains single stranded. In either case the double stranded portion of the promoter-primer comprises a RNA polymerase promoter sequence, whereas the single stranded portion comprises a sequence complementary to a 3' portion of the target region of a nucleic acid.

Figure 4:
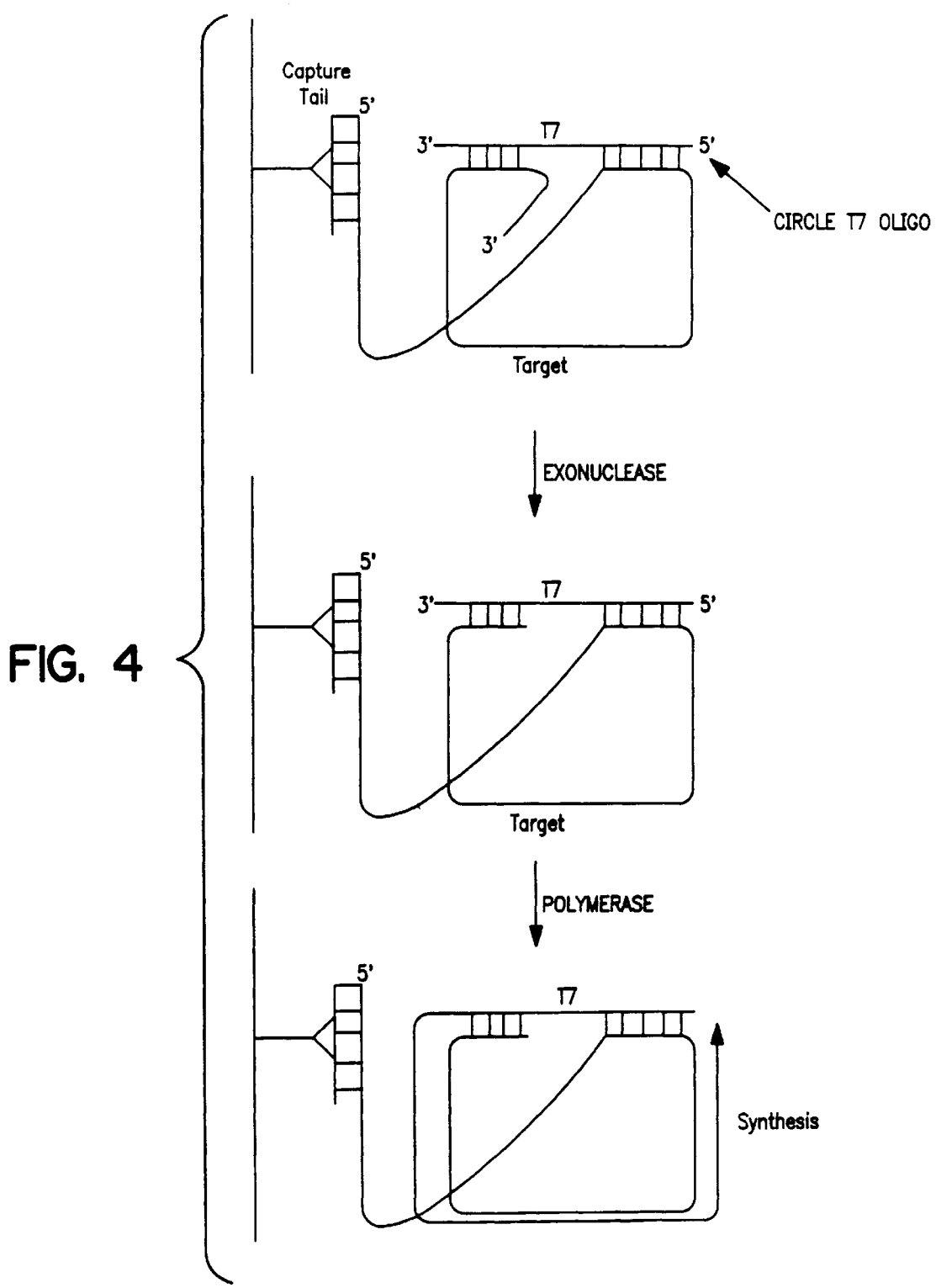
FIG. 4: Illustrative schematic of capture tail embodiment.
Figure 5:
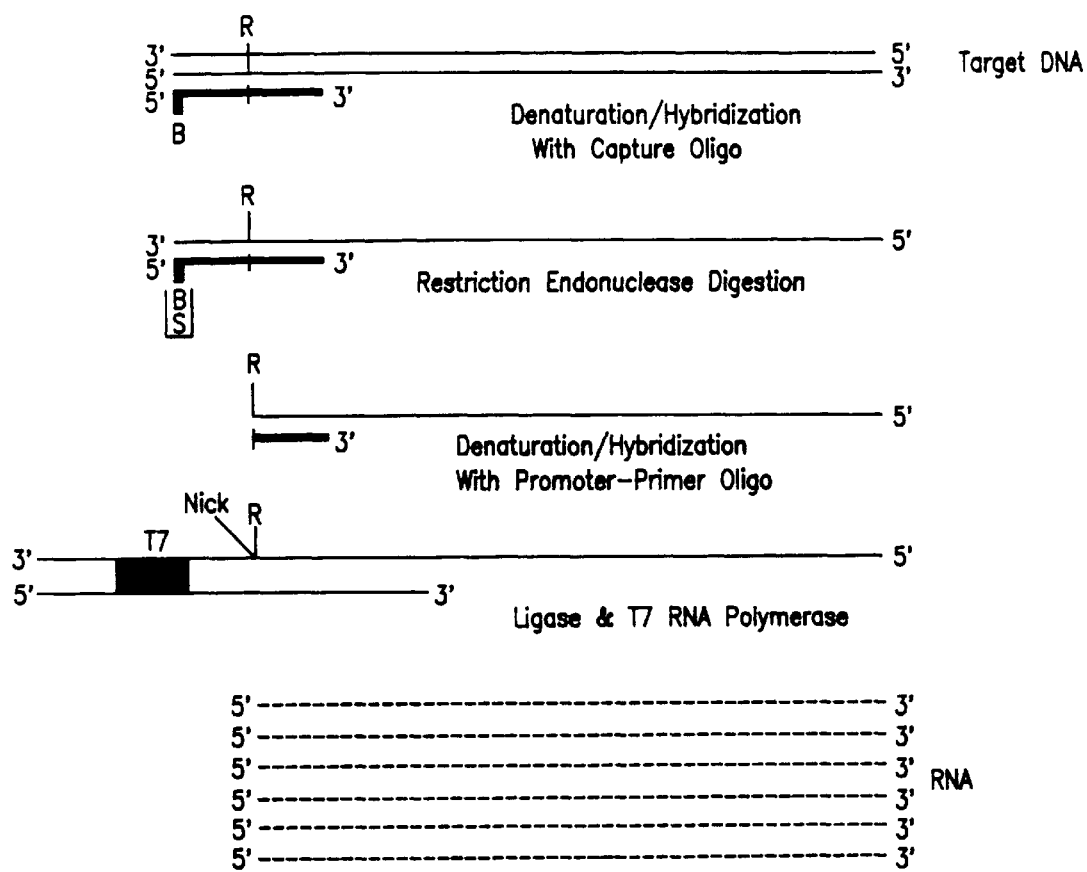
FIG. 5: Ligase CAR with a partially double-stranded promoter primer and restriction site trimming probe.
Figure 6:
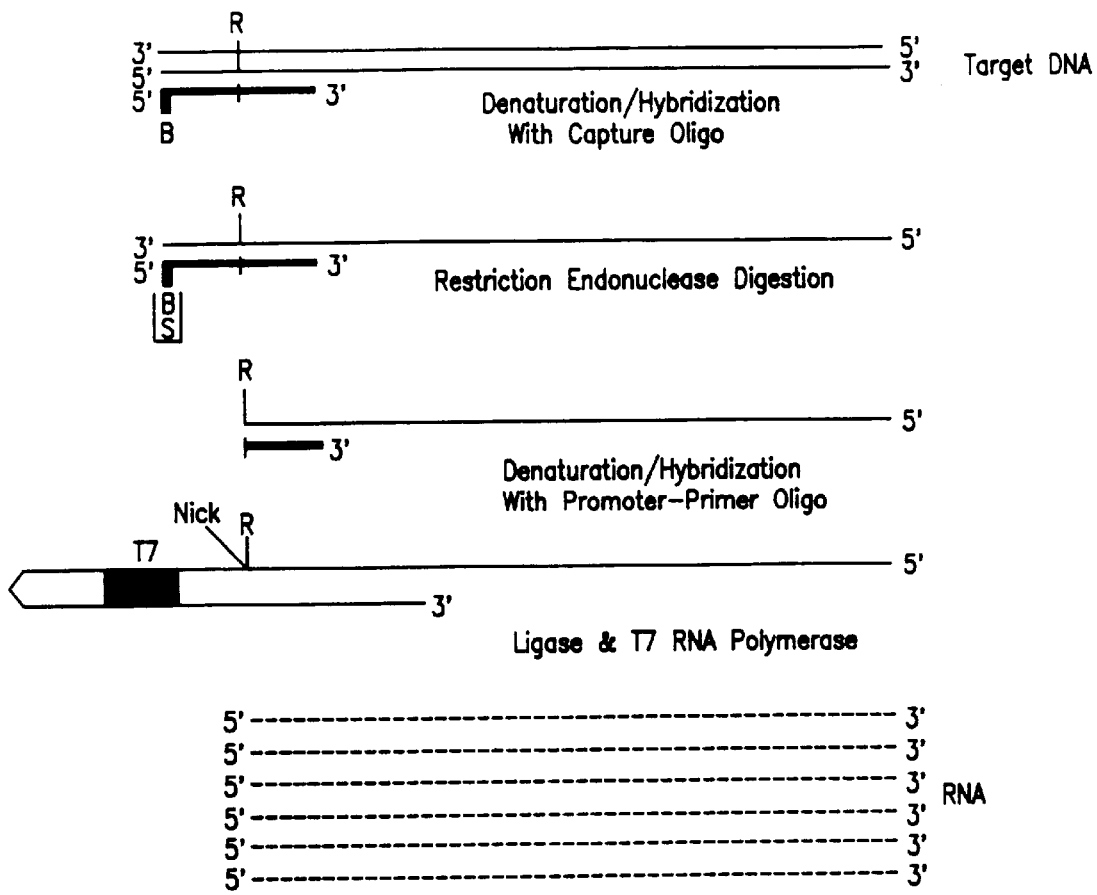
FIG. 6: Ligase CAR with loop promoter-primer and trimming probe.

In another embodiment of CAR, the single stranded (i.e. denatured) target DNA may be hybridized to a complementary oligonucleotide which is fixed to a solid matrix (see FIG. 4). This step may serve to separate the nucleic acid of interest from other molecules in a sample. If the target sequence has been hybridized to the immobilized oligonucleotide by its 5' flanking sequence, the immobilized target may then be hybridized with the promoter-primer of the present invention and the steps of amplification may be carried out as described above and herein below.

Denaturing a sample may be necessary to carry out the assay of the present invention in cases where the target nucleic acid is found in a double-stranded form or has a propensity to maintain a rigid structure. Denaturing is a step producing a single stranded nucleic acid and can be accomplished by several methods well-known in the art (Sambrook et al. (1989) in "Molecular Cloning: A Laboratory Manual," Cold Spring Harbor Press, Plainview, N.Y.). One preferred method for denaturation may be heat, for example 90–100° C., for about 2–20 minutes.

Alternatively, a base may be used as a denaturant when the nucleic acid is a DNA. Many known basic solutions are useful for denaturation, which are well-known in the art. One preferred method uses a base, such as NaOH, for example, at a concentration of 0.1 to 2.0 N NaOH at a temperature of 20–100° C., which is incubated for 5–120 minutes. Treatment with a base, such as sodium hydroxide not only reduces the viscosity of the sample, which in itself increases the kinetics of subsequent enzymatic reactions, but also aids in homogenizing the sample and reducing background by destroying any existing DNA-RNA or RNA-RNA hybrids in the sample.

The target nucleic acid molecules are hybridized to a promoter-primer complementary to the target region of a nucleic acid. Hybridization is conducted under standard hybridization conditions well known to those skilled in the art. Reaction conditions for hybridization of an oligonucleotide promoter-primer to a nucleic acid sequence vary from oligonucleotide to oligonucleotide, depending on factors such as oligonucleotide length, the number of G and C nucleotides, and the composition of the buffer utilized in the hybridization reaction. Moderately stringent hybridization conditions are generally understood by those skilled in the art as conditions approximately 25° C. below the melting temperature of a perfectly base-paired double stranded DNA. Higher specificity is generally achieved by employing incubation conditions having higher temperatures, in other words more stringent conditions. Chapter 11 of the well-known laboratory manual of Sambrook et al., MOLECULAR CLONING: A LABORATORY MANUAL, second edition, Cold Spring Harbor Laboratory Press, New York (1990) (which is incorporated by reference herein), describes hybridization conditions for oligonucleotide probes and primers in great detail, including a description of the factors involved and the level of stringency necessary to guarantee hybridization with specificity.

The promoter-primers and target nucleic acids are incubated for approximately 5 to 120 minutes at about 20 to 80° C. to allow hybridization. Preferably, promoter-primer and target nucleic acid are incubated for about 20 to 60 minutes at about 30 to 70° C. Most preferably, the promoter-primer and target nucleic acid in the sample are incubated for about 30 minutes at about 35–50° C.

Hybridization is typically performed in a buffered aqueous solution, for which the conditions of temperature, salts concentration, and pH are selected to provide sufficient stringency such that the promoter-primer will hybridize specifically to the target nucleic acid sequence but not any other sequence. Generally, the efficiency of hybridization between promoter-primer and target will be improved under conditions where the amount of promoter-primer added is in molar excess to the template, preferably a 1000 to $10^6$ molar excess. It is understood, however, that the amount of target nucleic acid in the test sample may not be known, so that the amount of promoter-primer relative to template cannot be determined with certainty.

Alternatively, if the target DNA has been treated with base, the promoter-primer is diluted in a probe diluent that also acts as a neutralizing hybridization buffer. In this manner, the pH of the sample can be kept between pH 6 and pH 9, which will favor the hybridization reaction and will not interfere with subsequent enzymatic reactions. Preferably, the neutralizing buffer is a 2-[bis(2-hydroxyethyl) amino] ethane sulfonic acid ("BES") (Sigma, St. Louis, Mo.) and sodium acetate buffer. Most preferably, the neutralizing hybridization buffer is a mixture of 2 M BES, 1 M sodium acetate, 0.05% of an antimicrobial agent, such as $NaN_3$, 5 mM of a chelating agent, such as EDTA, 0.4% of a detergent, such as Tween-20™ and 20% of a hybridization accelerator, such as dextran sulfate. The pH of the neutralizing hybridization buffer is between approximately 5 to 5.5.

The promoter-primer of the present invention comprises a promoter portion and a primer portion. The primer portion will vary in sequence depending upon the target sequence. The primer portion comprises a length of at least 8 bases and may be as long as desired, for example to maximize specificity of hybridization. The promoter portion may comprise any RNA polymerase promoter sequence known in the art such as those described by Chamberlin and Ryan (1982 In: *The Enzymes*. San Diego, Calif., Academic Press: 15:87–108) and Jorgensen, et al (1991 *J. Biol. Chem.* 266:645–655). Several RNA polymerase promoter sequences are preferred: these include but are not limited to promoters derived from SP6 (Zhou & Doetsch, 1993 *Proc. Natl. Acad. Sci. USA* 90:6601–6605), T7 (Martin & Coleman, 1987 *Biochemistry*, 26:2690–2696) and T3 (McGraw, et al., 1985 *Nucl. Acid. Res.*, 13:6753–6766). Preferred is an RNA promoter sequence derived from *Thermus thermophilus* (Wendt et al. 1990 *Eur. J. Biochem.*, 191:467–472; Faraldo et al. 1992 *J. Bact.*, 174:7458–62; Hartmann et al. 1987 *Biochem*, 69:1097–1104, Hartmann et al. 1991 *Nucl. Acids Res.* 19:5957–5964). The length of the promoter portion of the promoter-primer will vary depending upon the promoter sequence chosen. For example, the T7 RNA polymerase promoter may be as short as 25 bases in length to act as functional promoters, while other promoter sequences require 50 or more bases to provide a functional promoter.

The promoter-primer may be produced by any suitable method known in the art, including by chemical synthesis, isolation from a naturally-occurring source, recombinant production and asymmetric PCR (McCabe, 1990 In: *PCR Protocols: A guide to methods and applications*. San Diego, Calif., Academic Press, 76–83). It may be preferred to chemically synthesize the promoter-primer in one or more segments and subsequently link the segments. Several chemical synthesis methods are described by Narang et al. (1979 *Meth. Enzymol.* 68:90), Brown et al. (1979 *Meth. Enzymol.* 68:109) and Caruthers et al. (1985 *Meth. Enzymol.* 154:287), which are incorporated herein by reference. Alternatively, cloning methods may provide a convenient nucleic acid fragment which can be isolated for use as a promoter primer. The overall nucleic acid composition of the promoter-primer will vary depending upon the target nucleic acid chosen and the type of CAR employed. The length of the promoter-primer will also vary depending upon the target nucleic acid, the promoter chosen and the degree of hybridization specificity desired.

In producing the promoter-primer of the present invention it may be desirable to modify the nucleotides or phosphodiester linkages in one or more positions of the promoter primer. For example, it may be advantageous to modify at least the 3' portion of the promoter-primer. Such a modification prevents the exonuclease activity from digesting any portion of the promoter-primer. It is preferred that at least the ultimate and penultimate nucleotides or phosphodiester linkages be modified. One such modification comprises a phosphorothioate compound which, once incorporated inhibits 3' exonucleolytic activity on the promoter-primer. It will be understood by those skilled in the art that other modifications of the promoter-primer, capable of blocking the exonuclease activity can be used to achieve the desired enzyme inhibition.

The trimming step of the present invention may be carried out by various means. The most common method of trimming back 3' ends utilizes the enzymatic activity of exonucleases. In particular, specific directional exonucleases facilitate a 3'-5' trimming back of the target DNA-promoter primer hybrid. Such exonucleases are known within the art and include, but are not limited to, exonuclease I, exonuclease III and exonuclease VII. Preferred, however, is the 3'-5' exonuclease activity associated with many nucleic acid polymerases. Using such nucleic acid polymerases reduces the number of enzymes required in the reaction and provides the appropriate activity to trim back the free 3' flanking ends of the target DNA.

Alternatively, it may be preferred to use a trimming probe method. A trimming probe may be particularly useful in cases where a long single-stranded sequence 3' to the target region is generated upon hybridization of a nucleic acid with a promoter-primer. The trimming probe technique is carried out prior to hybridization with a promoter-primer.

A trimming probe comprises a single stranded oligonucleotide which contains sequence complementary to a 3' portion of the target region of the nucleic acid. The 3' junction further comprises a potential restriction endonuclease recognition site, but for the fact that it is only present as a single strand. Restriction endonucleases are enzymes which specifically recognize and cleave a nucleic acid sequence. The restriction endonuclease recognition sequences vary in length but require a double-stranded sequence. These recognition sites are well-known in the art. Similarly restriction endonucleases are numerous and are well-known in the art. Sambrook et al. (1990 Molecular Cloning: A Laboratory Manual, second edition, Cold Spring Harbor Press, N.Y.) provides a review of many restriction endonucleases and their recognition sequences and is incorporated herein by reference.

The trimming probe procedure requires hybridization of the single stranded target sequence to the trimming probe. Hybridization creates a short double-stranded region forming a functional restriction endonuclease recognition sequence. The restriction endonuclease is then able to digest the target sequence as defined by the restriction cleavage site. Preferably, this restriction digestion reaction produces a target region having a flushed 3' end.

Optionally, the trimming probe may also carry a ligand in one or more positions, capable of being captured onto a solid matrix. A ligand conjugated-trimming probe provides a convenient way of separating the target DNA from other molecules present in a clinical sample. Once the ligand conjugated-capture probe—target sequence hybrid is trapped on a solid matrix via the ligand, the solid matrix is washed thereby separating the hybrid from all other components in the sample. The washed immobilized hybrid is subjected to restriction endonuclease digestion. After digestion, the target sequence is released from the solid matrix while the 5' end of the probe remains immobilized on the solid matrix. A small denaturation step allows the remaining portions of the trimming probe to be removed and the target sequence can then be hybridized to a promoter-primer molecule for amplification.

Use of a trimming probe is particularly advantageous in ligase CAR in the situation where a 5' sequence flanks the target region.

Many known ligands may be used in the trimming probe, including vitamin derivatives antigen-antibody complexes, metal derivatives and the like. In one preferred embodiment, biotin is used as the ligand, wherein the trimming probe is tagged with biotin and the solid matrix is coated with a strong binding molecule, such as avidin, streptavidin, or their derivatives. Various combinations of ligand and ligand-binding agent are well known and may be used to capture the hybrid onto a solid matrix. For example, digoxigenin and anti-digoxigenin 2, 4-dinitrophenol (DNP) and anti-DNP may be used. Fluorogens, such as fluorescein, phycoerythrin, allo-phycocyanin, phycocyanin rhodamine, Texas red or other proprietary fluorogens may be used in combination with an anti-fluorogen specific antibody.

Solid matrices useful in capturing the ligand-conjugated probe are available to the skilled artisan. Solid phases useful to serve as a matrix for the present invention include but are not limited to polystyrene, polyethylene, polypropylene, polycarbonate or any solid plastic material in the shape of test tubes, beads microparticles, dip-sticks or the like. Additionally, matrices include, but are not limited to membranes, 96-well microtiter plates, test tubes and Eppendorf tubes. Solid phases also include glass beads, glass test tubes and any other appropriate shape made of glass. A functionalized solid phase such as plastic or glass which has been modified so that the surface carries carboxyl, amino, hydrazide or aldehyde groups can also be used. In general such matrices comprise any surface wherein a ligand-binding agent can be attached or a surface which itself provides a ligand attachment site.

The single stranded target nucleic acid is hybridized to a promoter-primer. Trimming, as described above is either carried out prior to or simultaneous with the extension step.

"Extension" as the term is used herein is the addition of nucleotides to the 3' hydroxyl end of a nucleic acid wherein the addition is directed by the nucleic acid sequence of a template. Most often the extension step is facilitated by an enzyme capable of synthesizing DNA from an oligonucleotide primer and a template. Suitable enzymes for these purposes include, but are not limited to, for example, *E. coli* DNA polymerase I, Klenow fragment of *E. coli* DNA polymerase I, T4 DNA polymerase, Vent™ (exonuclease plus) DNA polymerase, Vents (exonuclease minus) DNA polymerase, Deep Vent™ (exonuclease plus) DNA polymerase, Deep Vents (exonuclease minus) DNA polymerase, 9°N$_m$ DNA polymerase (New England BioLabs), T7 DNA polymerase, Taq DNA polymerase, Tfi DNA polymerase (Epicentre Technologies), Tth DNA polymerase, Replitherm™ thermostable DNA polymerase and reverse transcriptase. One or more of these agent may be used in the extension step of CAR. To maximize efficiency, it may be desirable to use one agent for both the extension and trimming steps. Additional reagents may be added as necessary to shift the kinetic parameters of the polymerase enzyme to either increase or decrease its extension rate and/or 3'-5' and 5'-3' exonucleolytic activity. The extension step produces a double-stranded nucleic acid having a functional promoter at its 5' end.

Once formed, the double-stranded extension product serves as a template for RNA transcript production.

Transcription of the double-stranded extension product or partially double stranded ligation product carrying a functional promoter sequence is facilitated by an RNA polymerase. Many such polymerases are known in the art, including, but not limited to SP6 RNA Polymerase, T7 RNA polymerase and T3 RNA polymerase. A preferred RNA polymerase is *Thermus thermophilus* derived RNA polymerase. One or more such RNA polymerases may be employed in the transcription step of the CAR method.

Under suitable reaction conditions, including the presence of the necessary reagents, the synthesis of RNA transcripts will occur continuously and in proportion to the amount of the nucleic acid sequence to be detected that was originally present in the test sample. Additional reagents may be added as necessary to prepare the desired quantity of RNA transcripts. These reagents may be used to shift the equilibrium of the transcription reaction to either increase or decrease the transcription rate and efficiency as desired. One such reagent, inorganic pyrophosphatase, may be used to increase transcription yields and minimize the effect of magnesium ion concentration in the transcription reaction (Cunningham & Ofengand, 1990 *BioTechniques,* 9:713–714). Preferably the synthesis of RNA transcripts will be carried out in the presence of a ribonuclease inhibitor, as for example vanadyl-ribonucleoside complexes or human placental ribonuclease inhibitor, in order to avoid possible degradation of the transcripts by any adventitious ribonuclease contaminant. (Berger, 1987, *Meth. Enzymol.,* 152:227; de Martynoff et al., 1990, *Biochem. Biophys. Res. Commun.* 93:645; Sheel et al., 1979, *Proc. Natl. Acad. Sci. USA* 76:4898). After the appropriate length of time has passed to produce the desired quantity of RNA transcripts, the reaction may be halted by inactivating the RNA polymerase in any known manner or separating the components of the reaction.

The amplification reaction of the present invention produces transcripts which may be detected using various methods. For example, the transcripts may be directly detectable by addition of a labeled nucleotide in the transcription reaction. In many situations, it may be preferred to use label dUTP, since this nucleotide is specific to RNA molecules and hence its incorporation will be limited to transcription reaction products.

Many different labels may be used in generating detectable transcripts. Preferred methods of labeling RNA transcripts are with $^{32}$P or $^{35}$S using RNA polymerases. In addition, there are known non-radioactive techniques for signal amplification including methods for attaching chemical moieties to pyrimidine and purine rings (Dale, R. N. K. et al. (1973) *Proc. Natl. Acad. Sci. USA,* 70:2238–2242; Heck, R. F. (1968) *S. Am. Chem. Soc.,* 90:5518–5523), methods which allow detection by chemiluminescence (Barton, S. K. et al. (1992) *J. Am. Chem. Soc.,* 114:8736–8740) and methods utilizing biotinylated nucleic acid probes (Johnson, T. K. et al. (1983) *Anal. Biochem.,* 133:125–131; Erickson, P. F. et al. (1982) *J. of Immunology Methods,* 51:241–249; Matthaei, F. S. et al (1986) *Anal. Biochem.,* 157:123–128) and methods which allow detection by fluorescence using commercially available products.

Alternatively, nucleic acid probes may be used to detect CAR-produced RNA transcripts. Nucleic acid probes are detectable nucleic acid sequences that hybridize to complementary RNA or DNA sequences in a test sample. Detection of the probe indicates the presence of a particular nucleic acid sequence in the test sample for which the probe is specific. In addition to aiding scientific research, DNA or RNA probes can be used to detect the presence of viruses and microorganisms such as bacteria, yeast and protozoa as well as genetic mutations linked to specific disorders in patient samples. Grunstein et al., *Proc. Natl. Acad. Sci. USA* 72:3961 (1975) and Southern, *J. Mod. Biol.* 98:503 (1975) describe hybridization techniques using radiolabelled nucleic acid probes. Nucleic acid hybridization probes have the advantages of high sensitivity and specificity over other detection methods and do not require a viable organism. Hybridization probes are often labelled with a substance that can be easily detected. For example, a radioactive hybridization assay for human papillomavirus (HPV) is currently commercially available as a Profile™ kit from Digene Diagnostics (Silver Spring, Md.).

Hybridization can also be detected with the aid of an antibody specific for a labelled probe as described in U.S. Pat. No. 4,743,535 to Carrico. The probe is labelled with a detectable substance such as flavin adenine dinucleotide (FAD) or a fluorescent agent. An antibody specific for the labelled probe, after it has hybridized to the sample nucleic acid, is detected by a biochemical reaction.

Unlabeled transcripts may also be detected in the present invention. These transcripts may be detected by many techniques known in the art. For example, hybridization assays for the detection of RNA have been developed. For example, a hybridization protection assay for RNA is commercially available from Gen-Probe Inc. (San Diego, Calif.). The hybridization protection assay employs a single-stranded nucleic acid probe linked to an acridinium ester, as described by Engleberg, N. C., *ASM News* 57:183–186 (1991), Arnold et al. *Clin. Chem.* 35:1588–1594 (1989) and U.S. Pat. No. 4,851,330. Hybridization of the probe to a target RNA molecule protects the acridinium ester bond from base hydrolysis so that the detected chemiluminescent signal is proportional to the amount of target RNA in the sample.

Transcripts may also be subjected to a reverse transcriptase reaction in order to generate cDNAs which may be analyzed. For example such cDNA copies of transcripts may be analyzed for the presence of mutations. Mutational analysis includes but is not limited to, point mutations, deletions and insertions. These mutations can be detected by methods which are well-known in the art such as direct DNA sequencing (Maxam & Gilbert, 1980 *Methods Enzymol.* 65:499–559; Sanger, et al., 1977 *Proc. Natl. Acad. Sci. USA,* 74:5463–5467) and single-strand conformation polymorphism (SSCP) analysis (Leone, et al., 1993 *Oncogene,* 8:855–865). Furthermore, transcripts can be directly sequenced by using reverse transcriptase with appropriate oligodeoxyribonucleotide primers and chain terminating dideoxynucleotides (Mierendorf & Pfeffer 1987 *Methods. Enzymol.*, 15:563–566). Any reverse transcriptase can be used to perform this activity, preferably one which lacks RNase H activity, such as SuperScript II™ RNase H (Life Technologies). Lack of RNase H activity eliminates degradation of RNA molecules during the first strand cDNA synthesis, thus enabling the RNA template to be sequenced directly.

DNA probes used to detect CAR-produced RNA transcripts are synthesized or isolated in accordance with methods well known in the art as described by Sambrook et al., MOLECULAR CLONING: A LABORATORY MANUAL, COLD SPRING HARBOR LABORATORY, Cold Spring Harbor, N.Y. (1990). The probes can be double or single-stranded DNA molecules. A double-stranded DNA probe must first be denatured in base or with heat so that it becomes single-stranded prior to hybridization to the target RNA transcripts. If base is used to denature the double-stranded probe, then it is preferred that the base is sodium hydroxide in a concentration of between 0.1 and 2.0 M, and is incubated with the probe at a temperature between 20 and 100° C. for a period of between 5 and 120 minutes. More preferably, the base is 1.25 N NaOH and is incubated with the probe for ten minutes at room temperature. If heat is used to denature the probe, then it is preferred that the probe is incubated at 90–100° C. for a period between 5 and 100 minutes. More preferably, the probe is heated at a temperature of 90–100° C. for 10–15 minutes.

In order to avoid renaturation of the denatured DNA probe, the RNA transcript is preferably diluted in a neutralizing buffer, or neutralizing probe diluent, and the diluted RNA is then added to the denatured DNA probe to simultaneously neutralize the base and expose the target RNA to the denatured DNA probe for hybridization. It will be understood by those skilled in the art that a neutralizing probe diluent is defined herein as a buffer that will effectively neutralize the base. Numerous neutralizing buffers are well known to those skilled in the art. Preferably, the neutralizing probe diluent is a 2-[bis(2-Hydroxyethyl) amino] ethane sulfonic acid and sodium acetate buffer (BES/sodium acetate buffer).

Base or heat treatment is not required for single-stranded DNA probes. However, because single-stranded DNA probes are usually circular molecules, having been produced from a phage such as M13 bacteriophage, base treatment of the circular DNA nicks the circles, resulting in linear single-stranded DNA probes that generally produce improved hybridization.

The DNA detection probe may be labelled with a ligand and the ligand-labelled RNA:DNA hybrid is captured onto a solid phase coated with a substrate to which the ligand will bind with specificity. The captured hybrid is then detected as described in more detail below.

It will be understood by those skilled in the art that a solid phase includes polystyrene, polyethylene, polypropylene, polycarbonate or any solid plastic material in the shape of test tubes, beads, microparticles, dip-sticks or the like. A solid phase also includes glass beads, glass test tubes and any other appropriate shape made of glass. A functionalized solid phase such as plastic or glass that has been modified so that the surface contains carboxyl, amino, hydrazide or aldehyde groups can also be used. Therefore, any solid phase such as plastic or glass microparticles, beads, dip-sticks, test tubes or, preferably, microtiter plates can be used.

Any DNA probe used in the present invention may be labelled with at least one ligand by methods well-known to those skilled in the art including, for example, nick-translation, chemical or photochemical incorporation, and the incorporation of a ligand labelled primer into an amplified product such as a PCR product. In addition, the DNA probe may be labeled at multiple positions with one or multiple types of labels. Preferably, the DNA probe and capture probe are labelled with biotin, which binds to streptavidin; digoxigenin, which binds to anti-digoxigenin; or 2,4-dinitrophenol (DNP), which binds to anti-DNP. Fluorogens can also be used to label the probes. Examples of fluorogens include fluorescein and derivatives, phycoerythrin, allo-phycocyanin, phycocyanin, rhodamine, Texas Red or other proprietary fluorogens. The fluorogens are generally attached by chemical modification and bind to a fluorogen-specific antibody, such as anti-fluorescein. It will be understood by those skilled in the art that the probe can also be labelled by incorporation of a modified base containing any chemical group recognizable by specific antibodies. Other labels and methods of labelling nucleotide sequences for capture onto a solid phase coated with substrate are well known to those skilled in the art. A review of nucleic acid labels can be found in the article by Landegren, et al., "DNA Diagnostics-Molecular Techniques and Automation", Science, 242:229–237 (1988), which is incorporated herein by reference.

Most preferably, the label is biotin, the biotin-DNA:RNA hybrids are captured on a streptavidin-coated solid phase, and the captured hybrid is detected with an anti-DNA-RNA alkaline phosphatase conjugate. Preferably, streptavidin-coated microtiter plates are used. These plates may be coated passively or purchased commercially from Xenopore (Saddle Brook, N.J.) or prepared using the methods outlined below for immobilization of anti-hybrid antibody.

The detection probe may be unlabelled and an anti-hybrid antibody, either polyclonal or monoclonal, may be immobilized on the solid phase. It will be understood by those skilled in the art that the immobilized antibody can be bound directly to the solid phase or indirectly by use of a primary binding antibody or protein, such as streptavidin or protein G, that is bound to the solid phase and which subsequently binds the anti-hybrid antibody, a derivatized anti-hybrid antibody, a functional fragment of the anti-hybrid antibody, or a derivatized functional fragment of the anti-hybrid antibody.

Excess DNA probe in the sample is preferably degraded by enzymatic treatment with RNAase-free DNAase, available from the Sigma Chemical Co., St. Louis, Mo.

Any anti-hybrid antibody may be used to capture the hybrid onto the solid phase so long as the antibodies are specific for a double-stranded RNA:DNA hybrid. Such polyclonal anti-RNA:DNA hybrid antibodies may be derived from goats immunized with an RNA:DNA hybrids. Hybrid-specific antibodies maybe purified from the goat serum by affinity purification against RNA:DNA hybrid immobilized on a solid support. Monoclonal antibodies prepared using standard techniques can be used in place of the polyclonal antibodies.

The RNA:DNA hybrid antibody for capture or detection is prepared by the method of Kitawaga, Y. and Stollar, B. D., *Mol. Immunology* 19:413–420 (1982) or according to the method set forth in U.S. Pat. No. 4,732,847, issued Mar. 22, 1988 to Stuart et al., both of which are incorporated herein by reference.

It will be understood by those skilled in the art that either polyclonal or monoclonal anti-hybrid antibodies can be immobilized on the solid phase in the present assay as described below.

The anti-hybrid antibody is immobilized onto a solid phase such as a test tube surface or a 96-well microtiter plate. Immobilization of the antibody can be direct or indirect. Preferably, the solid phase is directly coated with anti-hybrid antibody in accordance with methods known to those skilled in the art or briefly described below. The antibody can also be biotinylated and subsequently immobilized on streptavidin coated surfaces, or modified by other means to covalently bind to the solid phase. Solubilized biotinylated antibody can be immobilized on the streptavidin coated surfaces before capture of the hybridized samples as described below or in conjunction with the addition of the hybridized samples as described below or in conjunction with the addition of the hybridized samples to simultaneously immobilize the biotinylated antibody and capture the hybrids.

More preferably, the antibody is attached to the solid phase in accordance with the method of Fleminger, G., et al., *Appl. Biochem. Biotech.* 23:123–137 (1990), by oxidizing the carbohydrate portion of the antibody with periodate to yield reactive aldehyde groups. The aldehyde groups are then reacted with a hydrazide-modified solid phase such as MicroBind-HZ™ microtiter plates available from Dynatech Laboratories (Chantilly, Va.). Passive coating of the antibody according to the well known method of Esser, P., Nunc Bulletin No. 6 (Nov. 1988) (Nunc, Roskilde, Denmark) is also acceptable.

Alternatively, Ventrex Star™ tubes (Ventrex Laboratories Inc., Portland, Me.) are coated with streptavidin by the method of Haun, M. and Wasi, S., *Anal. Biochem.* 191:337–342 (1990). After binding of streptavidin, the biotinylated goat polyclonal antibody described above, or otherwise produced by methods known to those skilled in the art, is bound to the immobilized streptavidin. Following antibody binding, the solid matrix can be post-coated with a detergent such as Tween™-20 and sucrose to block unbound sites on the surface and stabilize the bound proteins as described by Esser, P., Nunc Bulletin No. 8, pp. 1–5 (Dec. 1990) and Nunc Bulletin No. 9, pp. 1–4 (June 1991) (Nunc, Roskilde, Denmark) and Ansari, et al. *J. Immunol. Methods* 84:117–124 (1985). Preferably, each surface is coated with between 10 ng and 100 µg biotinylated antibody. Most preferably each surface is coated with approximately 250 ng of biotinylated antibody.

As discussed below, the solid phase can be coated with functional antibody fragments or derivatized functional fragments of the anti-hybrid antibody.

The CAR-produced RNA:DNA probe hybrids are exposed to the solid phase, which has been coated with either a substrate that binds with specificity to the ligand or ligand-conjugated probe or an anti-hybrid antibody, as described above, for a sufficient amount of time to allow binding or capture of the hybrid by the immobilized antibodies or substrate. The hybrids are bound to the immobilized antibodies or substrate by incubation for about five minutes to about twenty-four hours at about 15° C. to 65° C. on a platform shaker with a shaking speed of 0 to 1500 rpm. Preferably, the incubation time is about 30 to about 120 minutes at about 20° C. to 40° C., with shaking at 300 to 1200 rpm. More preferably, capture occurs with incubation at one hour at room temperature with vigorous shaking on a rotary platform shaker with a rotary shaking speed between approximately 300 and 1000 rpm. It will be understood by those skilled in the art that the incubation time, temperature, and shaking can be varied to achieve alternative capture kinetics as desired.

Hybridization is detected by conventional means well known in the art such as with a direct labelled polyclonal or monoclonal antibody specific for the hybrid or a labelled antibody. Alternatively, if the probe is labelled with a ligand as described above in the preferred embodiment, the hybrid can be detected with either a labelled anti-hybrid antibody or a labelled substrate, such as a streptavidin-alkaline phosphate conjugate. In the preferred embodiment, the target RNA is hybridized to a labelled probe, the hybrid is captured onto a substrate-coated solid phase, and the captured hybrid is detected onto a substrate-coated solid phase, and the captured hybrid is detected with a labelled anti-hybrid antibody.

Most preferably, the label of the anti-hybrid antibody is an enzyme, a fluorescent molecule or a biotin-avidin conjugate and is non-radioactive. The label can then be detected by conventional means well known in the art such as a calorimeter, a luminometer, or a fluorescence detector. The preferred label is alkaline phosphatase.

Detection of captured hybrid is preferably achieved by binding the above-described conjugated anti-hybrid molecule to the hybrid during incubation. Surfaces are then washed with the above-described wash buffer to remove any excess conjugate. Preferably, five manual washes are performed using either an Eppendorf™ Repeat Pipettor with a 50 ml Combitip™ (Eppendorf, Hamburg, Germany), a Corning repeat syringe (Corning, Corning, N.Y.), a simple pump regulated by a variostat, or by gravity flow from a reservoir with attached tubing. Commercially available tube washing systems available from Source Scientific Systems (Garden Grove, Calif.) can also be used.

As described above, captured hybrid can also be detected with a direct labelled DNA probe, such as an enzyme-conjugated hybridization probe, or a hapten-modified probe that is subsequently detected by a labelled anti-hapten antibody.

Bound conjugate is subsequently detected by colorimetry or chemiluminescence as described at Coutlee, et al., *J. Clin. Microbiol.* 27:1002–1007 (1989). Preferably, bound alkaline phosphatase conjugate is detected by chemiluminescence with a reagent such as a Lumi-Phos™ S30 reagent (Lumigen, Detroit, Mich.) using a detector such as an E/Lumina™ luminometer (Source Scientific Systems, Inc., Garden Grove, Calif.) or an Optocomp I™ Luminometer (MGM Instruments, Harden, Conn.).

A further embodiment of the present invention relates to the CAR procedure carried out as an automated process. Such a procedure may use an automated device for carrying out hybridization, polymerase extension, transcription and detection reactions in one or more vessels. This process is capable of analyzing multiple samples sequentially or simultaneously. The process may be automated in such a way as to include the use of robotics, such as the Biomek 2000™ (Beckman Instruments, Fullerton, Calif.), Plato 3300™ or Plato 1300™ (Rosys, Wilmington, DE) or LABTECH™ (Biochem Immunosystems, Allentown, Pa.). An automated thermoregulator combined with robotics may be particularly advantageous in an automated system for CAR, which could use a system such as a Robocycler 96™ or Robocycler 40™ (Stratagene, LaJolla, Calif.). Other systems for automating the CAR method are known in the art and are within the scope of the CAR invention.

One non-radioactive CAR assay kit contains the necessary devices and reagents for performing a CAR amplification reaction and a non-radioactive hybridization assay, as described above including an appropriate sample collection device, such as a dacron swab for exfoliated cell sample collection; sample transport medium for stabilization of the sample during transport to the laboratory for analysis; a promoter-primer for a specific nucleic acid target; a trimming probe or at least one 3'-5' exonuclease or at least one polymerase having 3' exonuclease activity for trimming back any sequence 3' to the target region in a nucleic acid; one or more DNA polymerases; RNA polymerase(s); one or more probes specific for the transcript to be detected; neutralizing probe diluent; anti-hybrid antibody- or substrate-coated test tubes or microtiter wells; a nuclease such as RNase, preferably contained in a solution also containing a conjugated anti-hybrid antibody that can be detected by conventional means; and any necessary controls.

The kit should contain a negative control and a positive control for each detection probe. Preferably, the negative control is enzymatically prepared RNA of a sequence that is not complementary to the detection probe. The positive control preferably contains enzymatically prepared RNA that is complementary to the probe.

In general, the assay can be used to detect as little as 1 pg RNA per ml of specimen with a typical specimen volume of 100 μl.

The following examples illustrate use of the present amplification method and detection assay and kit. These examples are offered by way of illustration, and are not intended to limit the scope of the invention in any manner. All references described herein are expressly incorporated in toto by reference.

EXAMPLE 1

Synthetic Promoter

Figure 3:
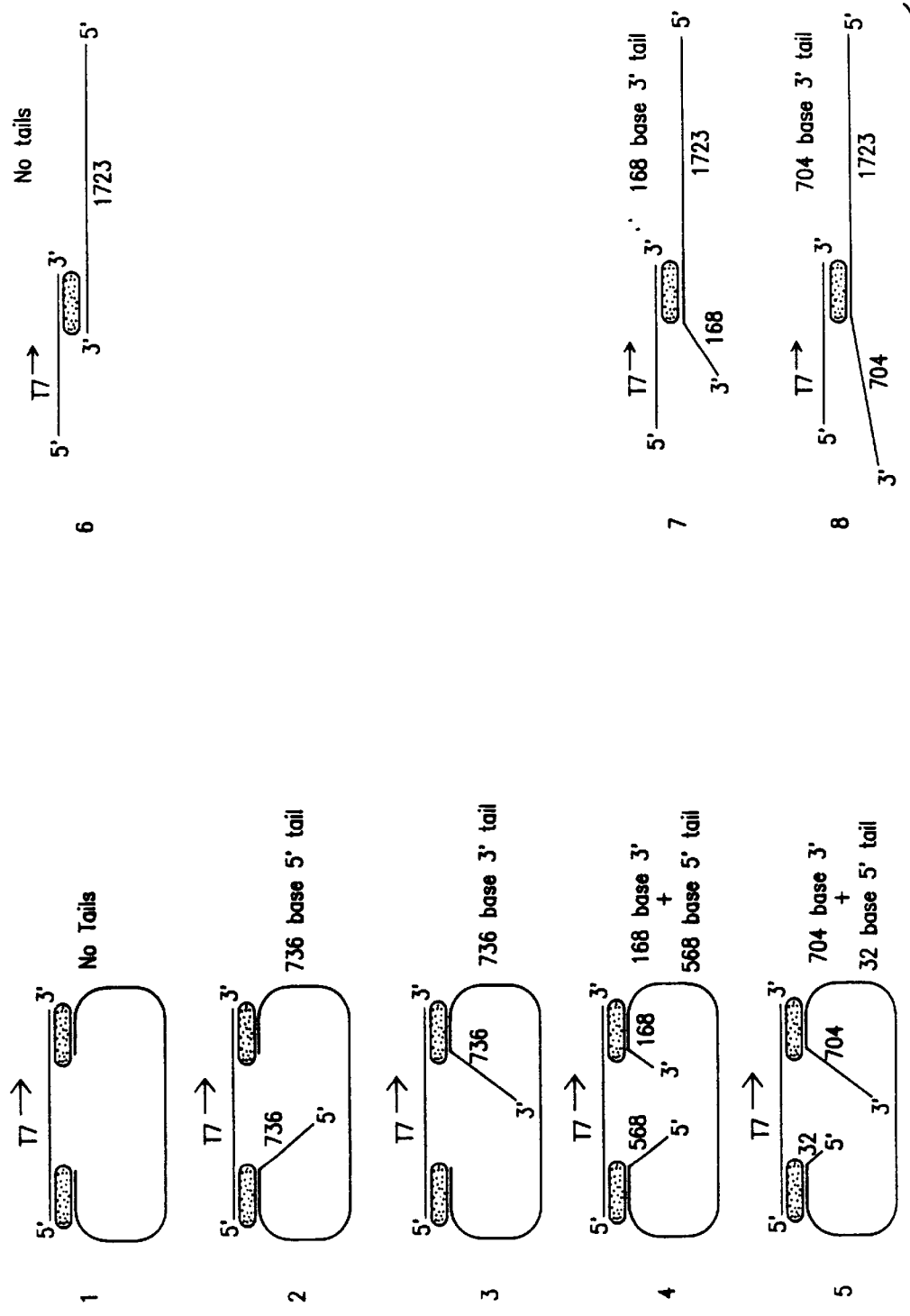
FIG. 3: Schematic Drawing of the various combinations of hybrids useful in CAR.

A 65 base oligonucleotide promoter-primer, containing the T7 RNA polymerase promoter core sequence and flanked by 20 base regions complementary to HIV-1, was chemically synthesized.

targets. The DNA used to generate the different targets is a 1181 bp Hind III fragment from the gag region of HIV-1. This fragment was subcloned from plasmid pNL4-3 (Adachi, et al. 1986, *J Virol* 59:284–291) into the Hind III site of pIC20H (Marsh, J. et al. 1984. *Gene* 32:481–485) to create plasmid pRK15 (FIG. 2). Digestion of plasmid pRK15 with different restriction endonucleases, followed by gel purification of the fragments, allows a variety of different target types to be formed. These are diagrammed in FIG. 3 and represent the structures generated after hybridization of the promoter-primer with each of the target fragments. Both linear and circular structures can be formed depending on the particular restriction endonuclease used to cut pRK15. For both linear and circular hybrid structures, any single stranded sequence 3' to the target region (also referred to herein as "3' end tails") may be removed by 3'→5' exonuclease prior to synthesizing a double stranded promoter region. Depending on the target DNA, the length of the 3' end tails were from 0 to 736 bases. The enzymes used to digest pRK15 to generate each of the targets is shown in Table 1.

TABLE 1

Profile of pRK15 Generated Targets for CAR.

| Target | Type | Enzyme(s) | 5' Tail length | 3' Tail Length |
|--------|----------|------------------|----------------|----------------|
| 1 | circular | Bgl II + Pst I | 0 | 0 |
| 2 | circular | Pst I | 736 | 0 |
| 3 | circular | Bgl II | 0 | 736 |
| 4 | circular | Nsi I | 568 | 168 |
| 5 | circular | Bss HII | 32 | 704 |
| 6 | linear | Pst I + Sca I | NA | 0 |
| 7 | linear | Nsi I + Sca I | NA | 168 |
| 8 | linear | Bss HII + Sca I | NA | 704 |

```
HIV-20 mer              T7 Promoter                 HIV-20 mer
                            +1
```
```
5'-AGTAAAGCCAGAGGAGATCTTAATACGACTCACTATAGGGAATTCCTGCAGAATGGGATAGATTG-3'
```

The HIV-1 regions of the promoter-primer are non-contiguous with respect to HIV and extend from base 665 to base 684 and base 1415 in the gag region of the genome (Adachi A, et al. 1986, *J. Virol* 59:284–291 [Accession #M19921]). The consensus sequence of the T7 RNA polymerase promoter region is well characterized (Oakley, J. L. and Coleman, J. E. 1977), *Proc. Natl. Acad. Sci. USA* 74:4266–4270; Dunn, J. J. and Studier, F. W. 1983 *J Mol Biol* 166:477–535) and is functional only when double-stranded (Milligan, J. F., et al. 1987. *Nuc Acids Res* 15:8783–8799). The single-stranded promoter-primer was therefore made into a duplex, by combined 3'→5' exonuclease/5'→3' DNA polymerase enzymatic activities, prior to RNA synthesis. The sequence of the promoter-primer oligonucleotide includes the T7 promoter conserved core region extending 17 bases upstream of the transcriptional initiation site (designated+1). The GGGA nucleotide sequence, immediately downstream of the 17 base core region, is the preferred site for transcription initiation (Milligan, J. F., et al. 1987, *Nuc Acids Res* 15:8783–8799). The nucleotides between the promoter region and the HIV-1 sequences generate an Eco RI restriction site that was inserted for convenience.

In order to illustrate the CAR method, a plasmid was constructed and modified to generate various DNA model

Hybridization and DNA Polymerase Reactions

Each of the targets (0, 5×10$^4$, 5×10$^6$, 5×10$^7$ or 5×10$^8$ molecules per reaction) were added to a hybridization mix comprising of 1×Vent™ polymerase buffer (New England Biolabs)(10 mM KCl, 10 mM (NH$_4$)SO$_4$, 20 mM Tris-HCl [pH 8.8], 2 mM MgSO$_4$ and 0.1% Triton-X-100), 55 nM of promoter-primer, 0.5 mM of each dNTP and 2 units of Vent™ (exo–) DNA polymerase (New England Biolabs), in a 15 μl final volume. The DNA was first denatured at 100° C. for 5 minutes, and later hybridized with the promoter-primer at 48° C. for 30 minutes. At the end of this period, 1 unit (1 μl) of Vent™ (exo+) DNA polymerase (NEB) was added to each tube. The tubes were then incubated for 30 minutes at 75° C. and the reactions terminated by diluting the samples to 100 μl with H$_2$O. The samples were then extracted with phenol/chloroform/iso-amyl alcohol (49.5/49.5/1) and further diluted with H$_2$O to 500 μl volumes. All DNA samples were concentrated to 10 μl final volumes with Microcon-30 filtration units (Amicon).

Transcription Reactions

The DNA samples (10 μl) were transcribed in 50 μl final volumes, each containing 10 mM DTT, 2 mM of each NTP, 40 mM Tris, pH 8.0, 8 mM $MgCl_2$, 75 mM NaCl, 100 μg/ml BSA, 5 units/μl RNAsin (Promega), 0.025 units/μl of inorganic pyrophosphatase (Sigma) and 6 units/μl of T7 RNA polymerase (Pharmacia). The transcription reactions were performed at 37° C. for two hours.

EXAMPLE 2

Detection of Amplified RNA Transcripts

A 5'-end biotinylated DNA probe was synthesized by polymerase chain reaction using a single biotinylated primer (positions 864–885 of Promega's pGEM3Z) and a non-biotinylated primer (position 180–202 of Promega's pGEM3Z). The DNA sequence of pRK15 and pGEM3Z are identical within these regions, but the former was used as the PCR template. Amplification was performed with the reagents from a Perkin-Elmer Cetus Gene Amp™ kit, 2 mM $MgCl_2$, and 0.5 AM of each primer, using a Perkin Elmer DNA Thermal Cycler. The thermal cycling profile used for PCR amplification involved an initial 3 minute denaturation step at 95° C., followed by 40 amplification cycles (1 minute at 94° C., 2 minutes at 55° C. and 2 minutes at 72° C.), and ended with a 10 minute extension at 72° C. The 704 base PCR generated product was purified using the Magic™ PCR Prep DNA Purification System (Promega).

Detection of CAR synthesized RNA was measured using a modification of the SHARP Signal™ System (Digene Diagnostics, Inc., Silver Spring, Md.). A 5 μl aliquot of biotinylated DNA was denatured in a mix containing 5 μl of SHARP™ sample diluent and 25 μl of SHARP™ denaturing reagent (Digene Diagnostics, Inc., Md.) at room temperature for 10 minutes. After initial incubation period, 25 μl of SHARP™ probe diluent (Digene Diagnostics, Inc., MD) was added to the reaction and the entire volume (60 μl) transferred into the transcription reaction sample tube. It is noted that the biotinylated DNA probe was present in the hybridization cocktail at a 1 nM final concentration. Hybridization was performed at 65° C. for 30 minutes. Following hybridization, the mixture was transferred to streptavidin coated plates and shaken for 30 minutes at 1100 rpm at room temperature. The mixture was decanted from the wells, 100 μl of SHARP™ detection reagent (Digene Diagnostics, Inc., MD) added and the plates were allowed to shake at 1100 rpm for 30 minutes at room temperature. The wells were then washed 5 times with SHARP™ wash solution (Digene Diagnostics, Inc., MD), twice with $H_2O$ and blotted on paper towels to remove excess liquid. Finally, 100 μl of SHARP™ substrate was added and the plates incubated at 37° C. for 1–12 hours before reading the absorbance at 410 nM in a plate reader (Bio-Rad).

EXAMPLE 3

Effect of 3' Tail and Template Type on CAR

The effects of the 3' tail and template type on CAR are summarized in Table 2. The background was represented by sample 1 which is the zero target control. Comparing the signal obtained from circular target (samples 2–6) with the obtained from linear target 6 (samples 7–11), or circular target 4 (samples 12–16) with linear target 7 (samples 7–21), indicates that there was no significant difference between linear and circular target amplification. However, when the signals from targets that lack 3' tails were compared with those obtained from the targets which required exonucleolytic removal of the 3' tail, a large difference in amplification was observed. The signal was approximately 100 fold less for those targets that have a 3' tail. These data indicate that exonucleolytic removal of the 3' tail, prior to synthesis of a double stranded promoter by DNA polymerase was limiting the reaction.

TABLE 2

Effect of 3' Tail and Template Type on CAR

| Sample | $A_{410}$ |
|---|---|
| 1. Probe without target | 0.003 |
| Target #1 (circular, no 3' tail) | |
| 2. $5 \times 10^8$ | **** |
| 3. $5 \times 10^7$ | **** |
| 4. $5 \times 10^6$ | **** |
| 5. $5 \times 10^5$ | 0.254 |
| 6. $5 \times 10^4$ | 0.053 |
| Target #6 (linear, no 3' tail) | |
| 7. $5 \times 10^8$ | **** |
| 8. $5 \times 10^7$ | **** |
| 9. $5 \times 10^6$ | **** |
| 10. $5 \times 10^5$ | 0.493 |
| 11. $5 \times 10^4$ | 0.013 |
| Target #4 (Circular, 168 base 3' tail) | |
| 12. $5 \times 10^8$ | **** |
| 13. $5 \times 10^7$ | 0.403 |
| 14. $5 \times 10^6$ | 0.029 |
| 15. $5 \times 10^5$ | 0.010 |
| 16. $5 \times 10^4$ | 0.009 |
| Target #7 (linear, 168 base 3' tail) | |
| 17. $5 \times 10^8$ | **** |
| 18. $5 \times 10^7$ | 0.281 |
| 19. $5 \times 10^6$ | 0.042 |
| 20. $5 \times 10^5$ | 0.011 |
| 21. $5 \times 10^4$ | 0.005 |

**** = signal > 2.5000

EXAMPLE 4

Effect of Alternative DNA Polymerases

There are several alternative combinations of DNA polymerases and exonucleases that can be used, either simultaneously or sequentially, to generate a functional double stranded promoter in the CAR method. Both thermostable and non-thermostable enzymes can be used depending on the reaction conditions. The primary requirement in this embodiment of the invention is that the promoter region remains non-functional, unless the specific target is present. As an alternative to the previously described methods, T7 DNA polymerase was used in place of Vent™ (exo+) DNA polymerase in the second step of the DNA synthesis reaction. The reaction conditions as described in Example 1 remained virtually unchanged, except for the changes which follow: Target 7 (see FIG. 3) was used at amounts from $5 \times 10^6$ to $5 \times 10^8$. This DNA/promoter-primer hybrid structure leaves a 3' tail (168 nucleotides long). In the first step of the hybridization reaction described in Example 1, Vent™ (exo−) DNA polymerase was replaced with Deep Vent™ (exo−) DNA polymerase (New England Biolabs). In the second step of the reaction, either no additional DNA polymerase was added and the reaction incubated at 75° C., or Deep Vent™ (exo+) DNA polymerase was added at 75° C., or T7 DNA polymerase was added and the reaction was incubated at 37° C.

The results are depicted in Table 3. The data indicates that using T7 DNA polymerase increases the signal 5 to 10 fold over that obtained with Deep Vents (exo+) DNA Polymerase. It can be hypothesized that T7 DNA polymerase has a higher, or more processive, 3'→5' exonuclease activity than Deep Vents (exo+) DNA polymerase, and was therefore able to remove the 3' tail more efficiently. Removal of the 3' tail enabled the 5'→3' polymerase activity of the enzyme to fill the complimentary strand, thus generating the double stranded T7 promoter region, which is ultimately required for successful transcription by T7 RNA polymerase.

TABLE 3

Effect of DNA Polymerase on CAR Activity.

| Sample | 2nd DNA Polymerase | $A_{410}$ |
|---|---|---|
| 1. $5 \times 10^8$ | none | 1.584 |
| 2. $5 \times 10^7$ | none | 0.199 |
| 3. $5 \times 10^6$ | none | 0.031 |
| 4. $5 \times 10^8$ | Deep Vent (exo+) | **** |
| 5. $5 \times 10^7$ | Deep Vent (exo+) | 0.519 |
| 6. $5 \times 10^6$ | Deep Vent (exo+) | 0.047 |
| 7. $5 \times 10^8$ | T7 DNA Polymerase | **** |
| 8. $5 \times 10^7$ | T7 DNA Polymerase | **** |
| 9. $5 \times 10^6$ | T7 DNA Polymerase | 0.490 |
| 10. 0 | none | 0.005 |

**** = signal > 2.5000
Hybridization and DNA polymerase reaction conditions have been optimized in a two step reaction. First, hybridization was performed in the presence of the Deep Vent ™ (exo−) DNA polymerase (first DNA polymerase). The lack of 3' exonuclease activity in this first step prevents degradation of the single stranded promoter, while at the same time, the hybridization process is enhanced by the extension of the 3' end of the promoter-probe during the annealing process (longer probe further stabilizes the hybrid). In the second step, or Deep Vent ™ (exo+) or T7 DNA polymerase is added. The 2nd DNA polymerase has 3'→5' exonuclease (removing the 3'-end tail) and 5'→3'polymerizing activity, resulting in the synthesis of double stranded DNA transcription targets.

CAR technology, using the previously mentioned T7 DNA polymerase method was repeated using less input target DNA. The results of this experiment are summarized in Table 4. These data reveal the ability of the system to easily detect $5 \times 10^5$ input DNA target molecules.

TABLE 4

Effect of Low Target Levels on CAR

| Sample | $A_{410}$ |
|---|---|
| 1. Probe without target | −0.12 |
| 2. $5 \times 10^7$ | **** |
| 3. $5 \times 10^6$ | 1.481 |
| 4. $5 \times 10^5$ | 0.187 |
| 5. $5 \times 10^4$ | 0.035 |
| 6. $5 \times 10^3$ | 0.010 |

**** = signal > 2.500

EXAMPLE 5

Hepatitis B Virus CAR Model System

The Human Hepatitis B Virus (HBV) genome is small, approx. 3200 bp, and composed of partially double-stranded DNA. The substrate for viral transcription in vivo is the complete (−) DNA strand. The (−) strand DNA is convenient to hybridize with a CAR promoter-primer due to the lack of a full (+) strand DNA. The fact that the entire DNA sequence of HBV is transcribed as a single message in vivo (which is detected via DNA:RNA hybrid formation), coupled with the above mentioned genomic features, makes HBV a suitable model target for CAR technology.

Synthetic Promoter

Two 75 base oligonucleotide promoter-primers, containing the T7 RNA polymerase promoter core sequence and flanked by 25 base regions complementary of HBV sequence were chemically synthesized.

```
Promoter-Primer HBV-32 (For circular CAR using the 1.6 kb
HBV

5'-P-CTCCCCGTCTGTGCCTTCTCATCTGTAATACGACTCACTATAGGGAATTCCAG
AGTCTAGACTCGTGGTGGAC-S-T-S-T3'

Promoter-Primer HBV-31 (For circular and linear CAR using
the entire genome of HBV)

5'-P-CTCCCCGTCTGTGCCTTCTCATCTGTAATACGACTCACTATAGGGAATTGATC
GCCGCGTCGCAGAAGATCTC-S-A-S-A-3'
```

Alignment of HBV DNA sequences from the major subtypes (adw2, adw, adr1, adr2, ayr, ayw1 and ayw2) indicated stretches of highly conserved nucleotide sequences which were used to generate the above CAR promoter-primers. The HBV regions of the promoter-primer are non-contiguous with respect to HBV and are conserved throughout all the major HBV DNA subtypes analyzed. This permitted amplification and detection of different HBV subtypes using the CAR method. The HBV sequences within the promoter-primer extended from base 1547 to base 1571 (X gene coding region) and base 224 to 268 (HBsAg coding region) of the genome for the HBV-32 promoter-32 promoter-probe, and from base 1547 to base 1571 (X gene coding region) and base 2415 to 2439 (HBcAg coding region) for the HBV-31 promoter probe (Anneke K. Raney and Alan McLachlan, The Biology Hepatitis B Virus, in *Molecular Biology of the Hepatitis B Virus*, Alan McLachlan, Eds., CRC Press Inc., Boca Raton, Fla., 1991, 5–13). The consensus sequence of the T7 RNA polymerase promoter region is well characterized (Oakley, J. L. and Coleman, J. E. 1977. *Proc. Nat'l. Acad. Sci. USA*

74:4266–4270; Dunn, J. J. and Studier, F. W. 1983. J Mol Biol 166:477–535) and is functional only when double-stranded (Milligan, J. F., et al. 1987. *Nuc Acids Res* 15:8783–8799). The single-stranded promoter-primer is preferably made into a duplex, by combined 3'→5' exonuclease/5'→3' DNA polymerase enzymatic activities, prior to DNA synthesis. The sequence of the promoter-primer oligonucleotide included the T7 promoter conserved core region extending 17 bases upstream of the transcriptional initiation site (designated+1). The GGGA nucleotide sequence, immediately downstream of the 17 base core region, is the preferred site for transcription initiation (Milligan, J. F., et al. 1987 *Nuc Acids Res* 15:8783–8799). The nucleotides between the promoter region and the HBV sequences generated an EcoRI restriction site that was inserted for convenience.

The 75-mer promoter-primers also had a 5'-end phosphate and 3'-end phosphorothioate linkages between the last, second to last and third to last nucleotides ("blocked ends"). The two tandem phosphorothioate linkages prevented 3'-5' exonucleolytic processive cleavage of the promoter-primers by the DNA polymerase without interfering with the 5'-3' polymerizing activity of the enzyme.

Using two different promoter-primers hybridized circles of different dimensions were generated, with 5'and/or 3' tails varying in length, depending on the size and sequence of the target DNA to be copied and transcribed via CAR.

EXAMPLE 6

In order to illustrate circular CAR, two plasmids were constructed and modified to generate various DNA targets. The DNA used to generate the different targets was a 1581 bp EcoRI/BsiHKAI fragment from HBV ayw and adw2 strains. After double digestion of pGEM3Z with EcoRI and PstI, these fragments were cloned into plasmid pGEM3Z (Promega) to create plasmids pADRAYW and pADRADW2 respectively. Digestion of plasmids PADRAYW and/or pADRADW2 with different restriction endonucleases, followed by gel purification of the fragments, allowed a variety of different target types to be formed. Both linear and circular structures can be formed depending on the particular restriction endonuclease used to cut PADRAYW and/or pADRADW2. For both linear and circular hybrid structures the 3' end tail of the target, if present, must be removed by a 3'→5' exonuclease prior to synthesizing a double stranded promoter region.

Hybridization, DNA Polymerase and RNA Polymerase Reactions (single buffer/single tube format)

The reaction buffer contained salts, DTT, four dNTPs (DATP, dGTP, dCTP, dTTP) four NTPs (ATP, GTP, CTP, UTP), one or more suitable RNase inhibitors and one or more suitable carrier proteins. The final reaction volume was 25 $\mu$l and contained the reaction buffer, target DNA ($10^9$ molecules) and promoter-primer ($10^{13}$ molecules).

The reaction buffer, DNA and promoter-primer were mixed together and heated for 1 min. at 100° C. The heated mixture was then allowed to cool to 37° C. for 10 min. Five units of *E.coli* DNA polymerase I and 5 units of T7 RNA polymerase were added to the mixture, and incubation at 37° C. for two hours followed.

Detection of CAR synthesized RNA was performed by running the reactions on a denaturing formaldehyde gel and staining with ethidium bromide to visualize the products. Specific RNA transcripts were observed, thus demonstrating the applicability of the CAR method to the HBV model system.

Modifications and variations of the continuous amplification reaction and corresponding kits will be obvious to those skilled in the art from the foregoing detailed description of the invention. Such modifications and variations are intended to come within the scope of the appended claims.

We claim:

1. A method of amplifying a target nucleic acid comprising the steps of:
    providing a single-stranded nucleic acid containing a target region;
    hybridizing the target region of said nucleic acid to a promoter-primer having a central promoter portion and two regions homologous to non-contiguous portions of the target region forming a circular hybrid;
    trimming back single-stranded sequence 3'to the target region generating a flushed 3' end of said hybrid;
    extending 3' ends of the target region and the promoter-primer forming a double-stranded intermediate; and
    transcribing the double-stranded intermediate producing many RNA transcripts from each target region.

2. A method according to claim 1 further comprising:
    denaturing a double stranded nucleic acid, thereby providing a single-stranded nucleic acid.

3. A method according to claim 2 wherein denaturing comprises:
    treating said nucleic acid with a base; and
    neutralizing with a hybridization neutralization buffer.

4. A method according to claim 1 wherein the single stranded nucleic acid is hybridized to a capture probe.

5. A method according to claim 1 wherein the trimming and extending steps are carried out using at least one DNA polymerase having exonuclease activity.

6. A method according to claim 1 wherein the trimming and extending steps are carried out using at least one DNA polymerase and at least one exonuclease.

7. A method according to claim 1 wherein the promoter-primer comprises modified nucleotides or phosphodiester linkages in at least an ultimate 3' end position.

8. A method of detecting a nucleic acid containing a target region comprising the steps of:
    providing a single-stranded nucleic acid comprising said target region;
    hybridizing said nucleic acid to a single stranded promoter-primer having a 5' primer portion and a 3' promoter portion, said 3' primer portion comprising a sequence complementary to a 3' portion of said target region, said 3' primer portion further comprising at least one modified nucleotide or modified phosphodiester linkage to resist exonuclease activity, to form a hybrid;
    trimming back single-stranded sequence 3' to the target with an exonuclease activity, thereby generating a flushed 3' end of said hybrid;
    extending 3' ends of said target region and the promoter-primer forming a double-stranded intermediate;
    transcribing the double-stranded intermediate producing many RNA transcripts from each target region; and
    detecting RNA transcripts.

9. A method according to claim 8 further comprising:
    denaturing a double stranded nucleic acid, thereby providing the single-stranded nucleic acid.

10. A method according to claim 9 wherein denaturing comprises:
    treating said nucleic acid with a base; and
    neutralizing with a hybridization neutralization buffer.

11. A method according to claim 8 wherein the single stranded nucleic acid is hybridized to a capture probe.

12. A method according to claim 8 wherein the trimming and extending steps are carried out using at least one DNA polymerase having exonuclease activity.

13. A method according to claim 8 wherein the trimming and extending steps are carried out using at least one DNA polymerase and at least one exonuclease.

14. The method of claim 8 wherein the RNA transcripts are detected by a method comprising the steps of:
   a—hybridizing the RNA transcript to a complementary DNA probe to form a double-stranded hybrid;
   b—capturing the hybrid of step (a) onto a solid phase to form a bound hybrid;
   c—eliminating non-hybridized nucleic acid; and
   d—detecting the bound hybrid.

15. The method of claim 14 wherein the complementary DNA probe is labelled with at least one ligand.

16. The method of claim 14 wherein the DNA probe is biotinylated and the solid phase is coated with streptavidin.

17. The method of claim 14 wherein an anti-hybrid antibody or anti-hybrid fragment has been immobilized to the solid phase, wherein the antibody or antibody fragment specifically binds to a component of the double-stranded hybrid.

18. The method of claim 14 wherein the probe is double-stranded DNA, comprising the additional step of treating the probe with a base to form single-stranded DNA prior to the hybridization step.

19. A kit for amplification of nucleic acid in a biological sample comprising:
   a promoter-primer having a central promoter portion and two regions homologous to non-contiguous sequences in the target region;
   a trimming back agent;
   a nucleic acid polymerase;
   an RNA polymerase; and
   a sample transport medium for stabilization of the biological sample.

20. A kit for amplification of nucleic acid in a biological sample comprising:
   a promoter-primer having a 5' promoter portion and a 3' primer portion, said primer portion comprising a sequence complementary to a 3' portion of said target region, said promoter-primer further comprising at least one modified nucleotide or phosphodiester linkage to resist exonuclease activity;
   a trimming back agent comprising an exonuclease activity;
   a nucleic acid polymerase;
   a RNA polymerase; and
   a sample transport medium for stabilization of the biological sample.

21. A kit for amplification and detection of nucleic acid in a biological sample comprising the components of claims 19 or 20, further comprising the components of:
   a DNA detection probe complementary to the target RNA sequence for formation of a double-stranded nucleic acid hybrid;
   a neutralizing probe diluent for diluting and neutralizing the treated probe;
   a solid phase coated with a coating to which a hybrid formed by hybridization of the probe and the target nucleic acid sequence, will bind; and
   means for detecting the hybrid formed by hybridization of the probe and the target nucleic acid sequence.

22. The kit of claim 21 wherein the solid phase is coated with streptavidin and the probe is biotinylated.

23. The kit of claim 21 wherein the solid phase is coated with an anti-hybrid antibody or an anti-hybrid antibody fragment, wherein the antibody or antibody fragment specifically binds to a component of the double-stranded hybrid.

24. The kit of claim 21 further comprising a means for eliminating non-hybridized probe.

25. The kit of claim 21 wherein the detecting means is an anti-hybrid antibody or an anti-hybrid antibody fragment, wherein the antibody or antibody fragment specifically binds to a component of the double-stranded hybrid and is detectable.

26. The kit according to claim 24 wherein the means for eliminating non-hybridized probe is DNase.

* * * * *

UNITED STATES PATENT AND TRADEMARK OFFICE
CERTIFICATE OF CORRECTION

PATENT NO. : 5,981,179 Page 1 of 1
DATED : November 9, 1999
INVENTOR(S) : Attila T. Lorincz and Abel De La Rosa It is certified that error appears in the above-identified patent and that said Letters Patent is hereby corrected as shown below:

<u>Title page,</u>
Item [75], Inventors, "Attila T. Lorinez" and "Abel DeLaRosa" should read
-- Attila T. Lorincz -- and -- Abel De La Rosa --

Signed and Sealed this

Twenty-fourth Day of February, 2004

JON W. DUDAS
*Acting Director of the United States Patent and Trademark Office*